United States Patent [19]

Diamond et al.

[11] 4,061,771

[45] Dec. 6, 1977

[54] ETHYNYLINDENYL COMPOUNDS AND DERIVATIVES THEREOF USED IN THE TREATMENT OF PAIN, FEVER AND INFLAMMATION

[75] Inventors: Julius Diamond, Lafayette Hill; George H. Douglas, Paoli, both of Pa.

[73] Assignee: William H. Rorer, Inc., Fort Washington, Pa.

[21] Appl. No.: 709,438

[22] Filed: July 28, 1976

Related U.S. Application Data

[62] Division of Ser. No. 433,677, Jan. 16, 1974, Pat. No. 3,983,253, which is a division of Ser. No. 306,702, Nov. 15, 1972, Pat. No. 3,810,944.

[51] Int. Cl.² ................... A61K 31/275; C07C 121/50
[52] U.S. Cl. ................ 424/304; 260/465 E; 260/465 F; 260/465 G; 260/465 K; 260/576; 260/578; 260/604 R; 260/645; 260/646; 260/649 R; 424/330; 424/337; 424/349; 424/351
[58] Field of Search ............... 424/330, 337, 304, 349, 424/353; 260/576, 699 R, 465 E–465 G, 465 K, 645, 646, 807 A, 649 R

[56] References Cited

U.S. PATENT DOCUMENTS

| 3,681,436 | 8/1972 | Lynch et al. | 260/479 R |
|---|---|---|---|
| 3,810,944 | 5/1974 | Diamond et al. | 260/612 R |
| 3,983,253 | 9/1976 | Diamond et al. | 424/340 |

*Primary Examiner*—Leonard Schenkman
*Attorney, Agent, or Firm*—Erich M. H. Radde

[57] ABSTRACT

Novel ethynylindenyl compounds and derivatives are described. Their use in the treatment of inflammation is also disclosed.

39 Claims, No Drawings

ETHYNYLINDENYL COMPOUNDS AND DERIVATIVES THEREOF USED IN THE TREATMENT OF PAIN, FEVER AND INFLAMMATION

This is a division of application Ser. No. 433,677, filed Jan. 16, 1974, now U.S. Pat. No. 3,983,253 which is a division of Ser. No. 306,702, filed Nov. 15, 1972, now U.S. Pat. No. 3,810,944.

SUMMARY OF THE INVENTION

This invention describes novel indenylacetylenic compounds and derivatives and their use in therapeutic compositions. In addition, this invention describes the preparation of these indenylacetylenic compounds and their derivatives. When the compounds of this invention are administered to mammals, they afford significant treatment for the relief of inflammation and associated pain and fever.

BACKGROUND OF THE INVENTION

Continued studies have been carried out during the last decade to develop drugs which would significantly inhibit the development of inflammation and relieve pain and fever as well as the pain and fever associated with inflammation. While much of this effort has been carried out in the steroid field, there have been compounds developed which are non-steroidal.

In particular, there have been many compounds developed as analgesic and/or anti-inflammatory agents which are characteristically described because they are acidic in nature. One such group of compounds has been developed from an indenyl ring system which has a side chain consisting of an alkanoic acid or carboxylic acid derivative thereof such as an ester, amide or salt. The ring system may further be substituted, however, the acid side chain function is necessary for activity. While many of these compounds have been found to be effective, they have had the drawback of causing various side effects, in particular, gastric hemorrhage and ulceration.

We have unexpectedly found a series of compounds which has an indenyl ring system similar to those described above and have a high degree of pharmacological activity, however, they do not have this characteristic acidic side chain which has heretobefore been described as essentially associated with analgesic and anti-inflammatory properties.

We have unexpectedly found that when this alkanoic acid side chain or derivative of these molecules is replaced by an ethynyl moiety a group which is not a functional derivative of a carboxylic acid and which is chemically and physically unrelated, it unexpectedly results in compounds which have pronounced pharmacological properties and are unexpectedly useful for the relief and inhibition of inflammation conditions.

We have found that these ethynyl compounds are novel.

We have found that the compounds of this invention are effective in the treatment of inflammation and the control of arthritic conditions associated with inflammation without causing serious side effects.

We have further found that the compounds of this invention possess useful analgesic and antipyretic properties and are useful in the treatment of pain and/or fever without causing serious side effects.

We have further unexpectedly found that the compounds of this invention are pharmacologically effective with diminished gastric hemorrhage or ulceration as is commonly associated with those agents having the acidic side chain moiety present.

We have also found an entirely novel class of pharmaceutical compositions which contain the compounds of this invention as active ingredients.

We have still further found a novel process for the synthesizing of these compounds.

DESCRIPTION AND PREFERRED EMBODIMENTS

This invention comprises a class of chemical compounds which are effective for the relief and inhibition of inflammation and in the treatment of pain of fever. The compounds of this invention have the following generic formula I;

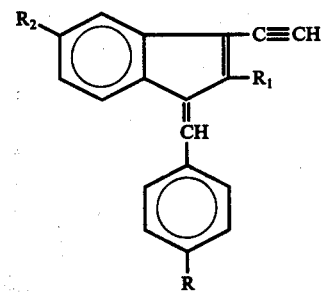

where
$R_1$ is hydrogen or loweralkyl;
R is halo, nitro, cyano, loweralkylsulfinyl or haloloweralkyl; and
$R_2$ is loweralkoxy, halo, nitro, loweralkyl, amino, or mono and diloweralkylamino.

The more preferred compounds of this invention are described by formula I where
$R_1$ is loweralkyl;
R is halo, nitro or loweralkylsulfinyl; and
$R_2$ is loweralkoxy, halo or diloweralkylamino.

The most preferred compounds are those where
$R_1$ is methyl;
R is chloro, bromo, fluoro, nitro or methylsulfinyl; and
$R_2$ is methoxy, fluoro or dimethylamino.

In the descriptive portions of this invention, the following definitions apply:

"Alkyl" refers to a loweralkyl hydrocarbon group containing from 1 to about 5 carbon atoms which may be straight chained or branched.

"Alkoxy" refers to a loweralkoxy group containing from about 1 to 5 carbon atoms which may be straight chained or branched.

The compounds of this invention may be prepared by the following general procedure:

Condensation of a substituted benzaldehyde with an α-bromoalkanoate in the presence of zinc dust can be carried out to result in the β-substitutedphenyl-β-hydroxy-α-alkylpropionate. This is preferably carried out in an inert atmosphere and in an inert solvent. The reaction is exothermic and can be controlled by the addition of the reactants. Treatment of this formed propionate with potassium hydrogen sulfate at increased temperatures eliminates water and forms the substituted α-alkylcinnamate. This reaction is preferably carried out in an inert solvent and the water formed is removed from the reaction mixture. Hydrogenation of the cinnamate over a suitable catalyst such as palladium on carbon results in the β-substitutedphenyl-α-alkylpropionate which is then ring closed with polyphosphoric acid at increased temperatures to result in the substituted-2-alkylindanone.

Etherification of the above indanone by triethylorthoformate in the presence of an acid catalyst such as a borontrifluoride; ether complex results in the substituted-2-alkyl-3-ethoxyindene.

Condensation of this later indene with the appropriately substituted benzaldehyde in the presence of a strong base catalyst and a polar medium leads to the 1-benzylidenylindene compound. Acid hydrolysis of the 3-ethylether results in this enolic 3-ketone which can be treated with the ethynyl Grignard to obtain the desired substituted-2-alkyl-1-benzylidenyl-3-ethynylindene.

The following reaction sequence illustrates this invention

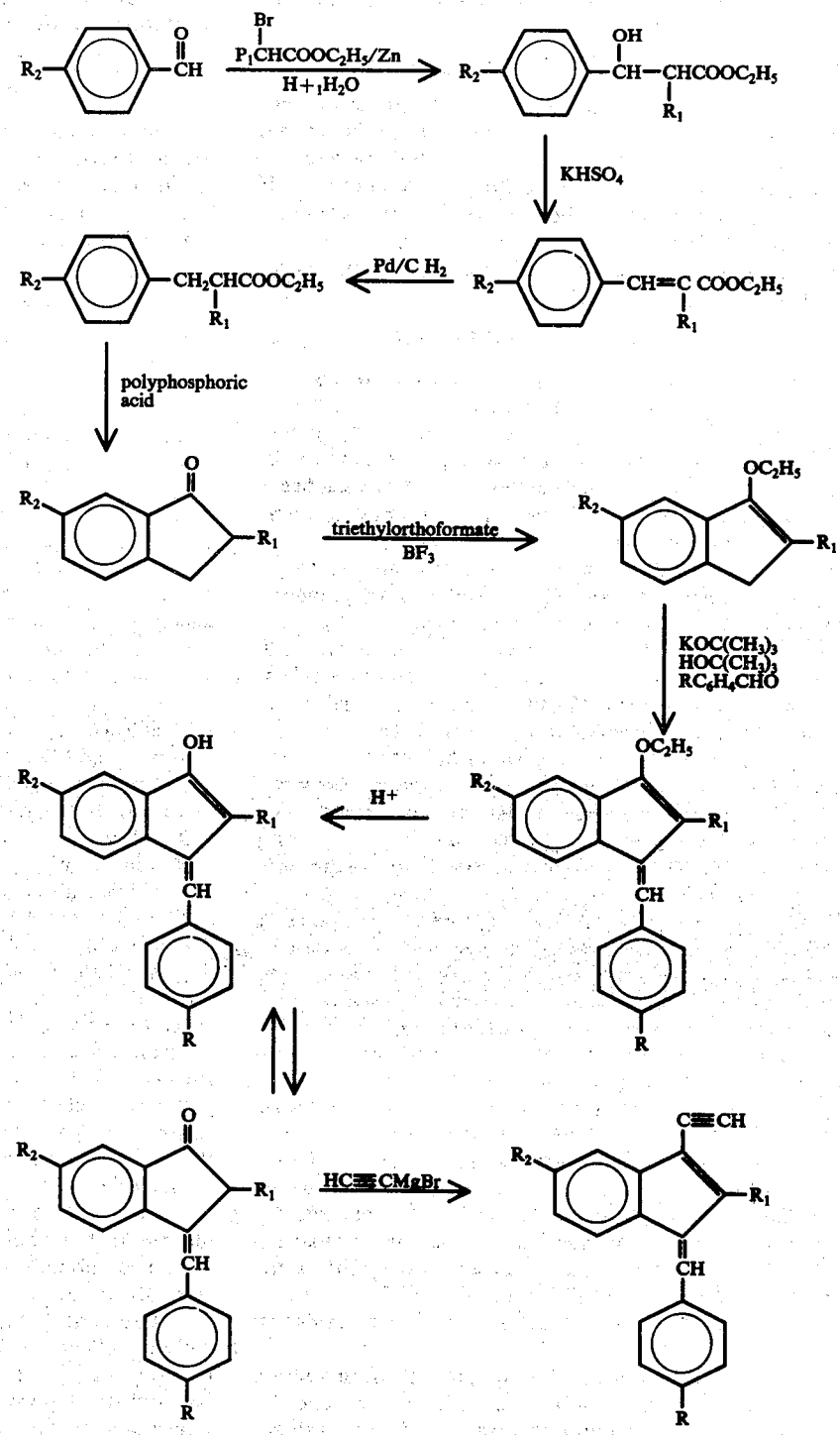

Appropriately desired end products having various R and $R_2$ substituents can be prepared at suitable stage of the synthesis by using suitable reactions in order to convert one group to another.

Thus, for example, a nitro group may be hydrogenated to the corresponding amine. This may then be mono- or dialkylated with loweralkyl halides or sulfates. It may also be reacted by diazotization to the diazonium fluoroborate which is then thermally decomposed to the fluoride. The amine may also be diazotized and heated in water or an alcohol to form the hydroxy or desired alkoxy group. Diazotization may also be carried out followed by a Sandmeyer type reactor to yield the halo groups of chloro, bromo or iodo. Diazotization followed by addition of cuprous cyanide results in the cyano compound. Diazotization followed by reaction with potassium ethylxanthate which is followed by hydrolysis yields the mercapto compound. This in turn can be alkylated and oxidized to the alkylthio, alkylsulfinyl and alkylsulfonyl groups. A halo compound such as the chloro, bromo or iodo may be reacted with trifluoromethyliodide and copper powder at about 150° C in dimethylformamide to obtain the trifluoromethyl compound.

I have found that the compounds of this invention exercise a useful degree of anti-inflammatory activity in mammals and are effective in the treatment of associated pain and fever and in the like conditions which are responsive to treatment with anti-inflammatory agents. In general, the compounds of this invention are indicated for a wide variety of mammalian conditions where the symptoms of inflammation and associated fever and pain are manifested. Exemplary of such conditions are: rheumatic diseases such as sciatica; pain and inflammation associated with dental surgery and similar human and veterinary disease conditions exhibiting the foregoing symptoms requiring the use of anti-inflammatory, analgesic and/or antipyretic agent.

I have also found that the compounds of this invention show a marked degree of analgesic activity and are effective in the relief of pain and fever. The compounds exhibit diminished gastric hemorrhage side effects.

For all the above purposes, the compounds of this invention are normally administered orally, topically, parenterally or rectally. Orally, these may be administered in tablets, capsules, suspensions or syrups; the optimum dosage, of course, depending on the particular compound being used and the type and severity of the condition being treated. In any specific case the appropriate dosage selected will further depend on factors of the patient which may influence response to the drug; for example, general health, age, weight, etc. Although the optimum quantities of the compounds of this invention to be used in such manner will depend on the compound employed and the particular type of disease condition treated, oral dose levels of preferred compounds when administered to a mammal in dosages of 0.5 to 100 milligrams per kilogram of body weight per day are particularly useful. The preferred range is 0.5 to 15 mg/kg. Comparative dosages may be used in topical, parenteral or rectal administration.

Dosage forms may be prepared according to any method known to the art for the manufacture of pharmaceutical compositions and such compositions may contain one or more agents; for example, sweetening agents, flavoring agents, coloring agents, preserving agents, etc. Further, the active acetylenic compounds may be administered alone or in admixture with antacids such as sodium bicarbonate, magnesium carbonate, magnesium hydroxide, aluminum hydroxide, magnesium silicate, etc., and non-toxic pharmaceutically acceptable excipients. Such excipients may be, for example, inert diluents such as calcium carbonate, lactose, etc., granulating and disintegrating agents; for example maize starch, alginic acid, etc., lubricating agents; for example, magnesium stearate, talc, etc., binding agents, for example, starch gelatin, etc., suspending agents; for example, methylcellulose, vegetable oil, etc., dispersing agents; for example, lecithin, etc., thickening agents; for example, beeswax, hard paraffin, etc., emulsifying agents; for example, naturally occurring gums, etc., and non-irritating excipients; for example, cocoa butter and polyethylene glycols.

Various tests in animals can be carried out to show the ability of the acetylenic compounds of this invention to exhibit reactions that can be correlated with anti-inflammatory activity in humans. One such test is the carrageenan paw edema test, which shows the ability of the instant compounds to inhibit edema induced by injection of an inflammatory agent such as carrageenan into the tissues of the paw of a rat against noninflammed controls. This carrageenan testing method is known to correlate well with anti-inflammatory activity in humans and is a standard test used to determine anti-inflammatory activity. This correlation can be shown by the activities of compounds known to be clinically active including such as aspirin, phenylbutazone, cortisone, hydrocortisone, indomethacin and prednisolone. In view of the results of this test, the acetylenic compounds of this invention can be considered to be active anti-inflammatory agents.

A further test to show the anti-inflammatory activity is the polyarthritis test in rats. This test is carried out on the animal model which closely resembles human arthritis and is widely used in the art. This is outlined by Winter & Nuss in *Arthritis and Rheumatism* 9: 394, (1966). In view of the results of this test, the acetylenic compounds of this invention can be considered to be active anti-inflammatory agents.

One method for measuring analgesic activity is the acetic acid writhing test as outlined by Siegmund et al in the *Proc. Soc. Exp. Biol. Med.* 95: 729–731, (1957). This method involves the intraperitoneal injection of 60 mg/kg of HOAc (0.6% solution; 0.1 ml/10 g) into male albino mice which produces a syndrome characterized by stretching movement. Analgesics prevent or suppress the stretch.

In view of the results of this test, the acetylenic compounds of this invention are considered to demonstrate non-narcotic analgesic activity.

One method of measuring gastric hemorrhage is as follows.

Albino male rats weighing 100–120 g are fasted for 24 hours but given free access to water. The animals are placed in groups of 10 animals per dose and dosed by gastric gavage at a volume of 1 ml/100 g body weight with test compound suspended in 0.5% methylcellulose. Four hours after administration of compound, the animals are sacrificed and the rumens of the stomachs assayed for gastric hemorrhage. Hemorrhage is defined as an area of blood which is 1 mm or larger at the largest diameter. Diameter of the hemorrhage is recorded. The number of animals in each group with stomachs having at least one area of hemorrhage is recorded. The presence of areas of blood smaller than 1 mm, defined as petechiae, is noted but not counted in the assay. The percent hemorrhage for each group is statistically analyzed to determine the dose magnitude ($ED_{50}$) which causes production of gastric hemorrhage in 50% of the animals.

The following are detailed examples which show the preparation of the compounds of this invention. They are to be construed as illustrations of said compounds and not as limitations thereof.

EXAMPLE 1

Ethyl β-(p-methoxyphenyl)-β-hydroxy-α-methylpropionate

To 36.2 g (0.55 mole) of purified zinc dust is added portionwise a solution of 80 g p-anisaldehyde (0.58 mole) in 80 ml of anhydrous benzene, 20 ml anhydrous ether and 98 g (0.54 mole) of ethyl 2-bromopropionate from a separatory funnel. About 15 ml of this solution is added to the zinc and the flask is warmed until the reaction starts and then heating is removed and allowed to continue exothermally. The addition takes about an hour. The reaction mixture is refluxed for 40 minutes and then cooled in an ice bath and hydrolyzed by the addition of 250 ml of cold 10% sulfuric acid with vigorous stirring. The acid layer is drawn off and the benzene solution is extracted twice with 63 ml of 5% sulfuric acid followed by 30 ml of 10% sodium carbonate solution, then with 3 × 30 ml of 5% sulfuric acid, and finally with 2 × 30 ml of water. The combined acid solution is extracted with 2 × 100 ml of ether and the combined ether and benzene solution is washed with 2 × 50 ml of saturated sodium chloride, then it is dried over sodium sulfate for 1½ hours and filtered. Most of the solvent is removed on an evaporator. The rest is distilled under vacuum to obtain ethyl β-(p-methoxyphenyl)-β-hydroxy-α-methylpropionate.

EXAMPLE 2

Ethyl p-methoxy-α-methylcinnamate

A mixture of 71.8 g (0.30 mole) of ethyl β-(p-methoxyphenyl)-β-hydroxy-α-methylpropionate is refluxed with 41.0 g (0.30 mole) of potassium hydrogen sulfate in 718 ml of benzene for 1 hour. The insoluble white crystals formed are filtered off, washed with benzene and the solvent of the filtrate is removed on evaporation. This is dissolved in 700 ml of ether. The ether solution is washed with 4 × 100 ml of cold water until neutral followed by 80 ml of saturated sodium chloride solution, then it is dried over magnesium sulfate for 1.5 hours and filtered. The solvent is removed on an evaporator to give ethyl p-methoxy-α-methylcinnamate.

EXAMPLE 3

Ethyl β-(p-methoxyphenyl)-α-methylpropionate

Ethyl p-methoxy-α-methylcinnamate (39.1 g) is dissolved in 186 ml of 2B ethanol. This solution is shaken with 1.5 g of 10% palladium on carbon at an initial pressure of 60 psi until the uptake of hydrogen is 100%. The reaction mixture is removed on an evaporator leaving ethyl β-(p-methoxyphenyl)-α-methylpropionate.

EXAMPLE 4

6-Methoxy-2-methylindanone

Ethyl β-(p-methoxyphenyl)-α-methylpropionate is added to 56 g of polyphosphoric acid with stirring at 50° C. The mixture is then heated to 83°-90° C for two hours. The cooled reaction mixture is poured slowly into a mixture of water and crushed ice with stirring and extracted with 3 × 300 ml of ether. The etheral solution is washed with 10% sodium bicarbonate solution followed by cold water to neutral, then with saturated sodium chloride solution and dried over magnesium sulfate for 1.5 hours and filtered. The solvent is removed on an evaporator and the residue distilled to obtain 6-methoxy-2-methylindanone.

EXAMPLE 5

2-Methyl-3-ethoxy-5-methoxyindene

6-Methoxy-2-methylindanone [1.76 g (0.01 mole)] is dissolved in 6.5 ml of absolute ethanol (containing 20% anhydrous ether). This solution is stirred with 2.4 g (0.016 mole) of triethylorthoformate and a drop of redistilled $BF_3C_2H_5OC_2H_5$ for about 72 hours. The reaction mixture is diluted with ether poured slowly into 8.1 ml. of 5.0% sodium hydroxide solution with crushed ice with stirring. Two layers separate and the organic layer is washed with cold water until neutral followed by saturated sodium chloride solution and dried over sodium sulfate. This is then filtered and the solvent removed and the residue distilled with 1 ml of benzene solution which contains about 47.5 mg of anhydrous p-toluene sulfonic acid to obtain 2-methyl-3-ethoxy-5-methoxyindene.

EXAMPLES 6-7

A. 1-(p-chlorobenzylidenyl)-2-methyl-3-ethoxy-5-methoxyindene

B. 2-methyl-3-(p-chlorobenzylidenyl)-6-methoxyindanone-1

A. 2-Methyl-3-ethoxy-5-methoxyindene [1.02 g (0.005 mole)] and p-chlorobenzaldehyde [0.74 g (0.005 mole)] are dissolved in 5 ml of t-butanol. To this solution is added 250 mg of potassium t-butoxide and the mixture is stirred at room temperature for five hours. The mixture is diluted with ether, poured slowly into cold water and the organic portion is washed with 7.5% sodium bicarbonate three times to get rid of stronger base. It is then dried over sodium sulfate briefly and filtered. The solvent is removed to give 1.45 g of 1-(p-chlorobenzylindenyl)-2-methyl-3-ethoxy-5-methoxyindene.

B. To 12 g of 1-(p-chlorobenzylindenyl)-2-methyl-3-ethoxy-5-methoxyindene in 120 ml of methanol is added an 18.5% hydrochloric acid solution and the reaction mixture is stirred at room temperature for three hours. The solid which separates is collected by filtration, washed with 70% methanol and recrystallized from methanol to obtain 2-methyl-3-(p-chlorobenzylidenyl)-6-methoxyindanone-1.

EXAMPLE 8

1-(p-chlorobenzylidenyl-2-methyl-3-ethynyl-5-methoxyindan-3-ol

A solution of 6.7 g of 2-methyl-3-(p-chlorobenzylidenyl)-6-methoxyindanone-1 is dissolved in 50 ml of tetrahydrofuran and is dropwise added into a solution of ethynyl magnesium bromide [prepared from 28 g (0.26 mole) of ethyl bromide in 180 ml of tetrahydrofuran]. The reaction mixture is stirred for 10 hours at room temperature. The solution is diluted with ether, poured slowly into saturated ammonium chloride solution and separated and extracted with benzene. This is then dried, filtered and the solvent removed to give a crude product. This is chromatographed on silica gel to give 1-(p-chlorobenzylidenyl)-2-methyl-3-ethynyl-5-methoxyindan-3-ol.

EXAMPLE 9

1-(p-chlorobenzylidenyl)-2-methyl-3-ethynyl-5-methoxyindene

A solution of 3.0 g of 1-(p-chlorobenzylidenyl)-2-methyl-3-ethynyl-5-methoxyindan-3-ol in 30 ml of benzene is added with stirring to anhydrous solution of 1.7 g of p-toluenesulfonic acid in 50 ml of benzene at room temperature. After five minutes, the crystalline solid is filtered off and the benzene solution is washed thoroughly with saturated sodium bicarbonate solution, then water, then dried over sodium sulfate. After filtration, the solution is evaporated, and the crude product crystallized from hexane/ether (10:1) to give 1-(p-chlorobenzylidenyl)-2-methyl-3-ethynyl-5-methoxyindene.

EXAMPLE 10

When p-anisaldehyde in Example 1 is replaced by the aldehydes of Table I below, then the corresponding product is prepared.

TABLE I

| | |
|---|---|
| p-ethoxybenzaldehyde | p-ethylvbenzaldehyde |
| p-propoxybenzaldehyde | p-propylbenzaldehyde |
| p-chlorobenzaldehyde | p-diethylamino |
| p-bromobenzaldehyde | p-dimethylamino |
| p-fluorobenzaldehyde | p-methylethylamino |
| p-nitrobenzaldehyde | p-methylisopropylamino |
| p-methylbenzaldehyde | |

EXAMPLE 11

When p-chlorobenzaldehyde in Example 6 is replaced by the aldehydes of Table II following, then the corresponding product is prepared.

TABLE II p-bromobenzaldehyde
p-fluorobenzaldehyde
p-nitrobenzaldehyde
p-cyanobenzaldehyde
p-methylthiobenzaldehyde
p-methylsulfinylbenzaldehyde
p-methylsulfonylbenzaldehyde
p-trifluoromethylbenzaldehyde

EXAMPLE 12

When ethyl 2-bromopropionate in Example 1 is replaced by ethyl bromoacetate then the corresponding product is prepared.

EXAMPLE 13

When the procedures of Examples 1–12 are followed the desired compound may be obtained by reacting the proper benzaldehydes. A representative list of the compounds thus obtained is shown below in Table III.

TABLE III 1-(p-bromobenzylidenyl)-2-methyl-3-ethynyl-5-methoxyindene
1-(p-fluorobenzylidenyl)-2-methyl-3-ethynyl-5-methoxyindene
1-(p-nitrobenzylidenyl)-2-methyl-3-ethynyl-5-methoxyindene
1-(p-cyanobenzylidenyl)-2-methyl-3-ethynyl-5-methoxyindene
1-(p-methylsulfinylbenzylidenyl)-2-methyl-3-ethynyl-5-methoxyindene
1-(p-trifluoromethylbenzylidenyl)-2-methyl-3-ethynyl-5-methoxyindene
1-(p-chlorobenzylidenyl)-2-methyl-3-ethynyl-5-ethoxyindene
1-(p-chlorobenzylidenyl)-2-methyl-3-ethynyl-5-propoxyindene
1-(p-chlorobenzylidenyl)-2-methyl-3-ethynyl-5-chloroindene
1-(p-chlorobenzylidenyl)-2-methyl-3-ethynyl-5-bromoindene
1-(p-chlorobenzylidenyl)-2-methyl-3-ethynyl-5-fluoroindene
1-(p-chlorobenzylidenyl)-2-methyl-3-ethynyl-5-nitroindene
1-(p-chlorobenzylidenyl)-2-methyl-3-ethynyl-5-methylindene
1-(p-chlorobenzylidenyl)-2-methyl-3-ethynyl-5-ethylindene
1-(p-chlorobenzylidenyl)-2-methyl-3-ethynyl-5-i-propylindene
1-(p-chlorobenzylidenyl)-2-methyl-3-ethynyl-5-aminoindene
1-(p-chlorobenzylidenyl)-2-methyl-3-ethynyl-5-ethylaminoindene
1-(p-chlorobenzylidenyl)-2-methyl-3-ethynyl-5-diethylaminoindene
1-(p-chlorobenzylidenyl)-2-methyl-3-ethynyl-5-dimethylaminoindene
1-(p-chlorobenzylidenyl)-2-methyl-3-ethynyl-5-methylethylaminoindene
1-(p-chlorobenzylidenyl)-2-methyl-3-ethynyl-5-methylisopropylindene
1-(p-bromobenzylidenyl)-2-methyl-3-ethynyl-5-diethylaminoindene
1-(p-fluorobenzylidenyl)-2-methyl-3-ethynyl-5-diethylaminoindene
1-(p-nitrobenzylidenyl)-2-methyl-3-ethynyl-5-diethylaminoindene
1-(p-cyanobenzylidenyl)-2-methyl-3-ethynyl-5-diethylaminoindene
1-(p-methylsulfinylbenzylidenyl)-2-methyl-3-ethynyl-5-diethylaminoindene
1-(p-trifluoromethylbenzylidenyl)-2-methyl-3-ethynyl-5-diethylaminoindene
1-(p-bromobenzylidenyl)-2-methyl-3-ethynyl-5-nitroindene
1-(p-fluorobenzylidenyl)-2-methyl-3-ethynyl-5-nitroindene
1-(p-nitrobenzylidenyl)-2-methyl-3-3-ethynyl-5-nitroindene
1-(p-cyanobenzylidenyl)-2-methyl-3-ethynyl-5-nitroindene
1-(p-methylsulfinylbenzylidenyl)-2-methyl-3-ethynyl-5-nitroindene
1-(p-trifluoromethylbenzylidenyl)-2-methyl-3-ethynyl-5-nitroindene
1-(p-bromobenzylidenyl)-2-methyl-3-ethynyl-5-fluoroindene
1-(p-fluorobenzylidenyl)-2-methyl-3-ethynyl-5-fluoroindene
1-(p-nitrobenzylidenyl)-2-methyl-3-ethynyl-5-fluoroindene
1-(p-cyanobenzylidenyl)-2-methyl-3-ethynyl-5-fluoroindene
1-(p-methylsulfinylbenzylidenyl)-2-methyl-3-ethynyl-5-fluoroindene 1-(p-trifluoromethylbenzylidenyl)-2-methyl-3-ethynyl-5-fluoroindene
1-(p-bromobenzylidenyl)-2-methyl-3-ethynyl-5-methylindene
1-(p-fluorobenzylidenyl)-2-methyl-3-ethynyl-5-methylindene
1-(p-nitrobenzylidenyl)-2-methyl-3-ethynyl-5-methylindene
1-(p-cyanobenzylidenyl)-2-methyl-3-ethynyl-5-methylindene
1-(p-methylsulfinylbenzylidenyl)-2-methyl-3-ethynyl-5-methylindene
1-(p-trifluoromethylbenzylidenyl)-2-methyl-3-ethynyl-5-methylindene
1-(p-bromobenzylidenyl)-2-methyl-3-ethynyl-5-chloroindene
1-(p-fluorobenzylidenyl)-2-methyl-3-ethynyl-5-chloroindene
1-(p-nitrobenzylidenyl)-2-methyl-3-ethynyl-5-chloroindene
1-(p-cyanobenzylidenyl)-2-methyl-3-ethynyl-5-chloroindene
1-(p-methylsulfinylbenzylidenyl)-2-methyl-3-ethynyl-5-chloroindene
1-(p-trifluoromethylbenzylidenyl)-2-methyl-3-ethynyl-5-chloroindene
1-(p-chlorobenzylidenyl)-3-ethynyl-5-methoxyindene
1-(p-nitrobenzylidenyl)-3-ethynyl-5-methoxyindene
1-(p-methylsulfinylbenzylidenyl)-3-ethynyl-5-methoxyindene
1-(p-trifluoromethylbenzylidenyl)-3-ethynyl-5-methoxyindene
1-(p-chlorobenzylidenyl)-3-ethynyl-5-ethoxyindene
1-(p-chlorobenzylidenyl)-3-ethynyl-5-chloroindene
1-(p-chlorobenzylidenyl)-3-ethynyl-5-fluoroindene
1-(p-chlorobenzylidenyl)-3-ethynyl-5-nitroindene
1-(p-chlorobenzylidenyl)-3-ethynyl-5-methylindene
1-(p-chlorobenzylidenyl)-3-ethynyl-5-diethylaminoindene
1-(p-fluorobenzylidenyl)-3-ethynyl-5-diethylaminoindene
1-(p-nitrobenzylidenyl)-3-ethynyl-5-diethylaminoindene
1-(p-cyanobenzylidenyl)-3-ethynyl-5-diethylaminoindene
1-(p-methylsulfinylbenzylidenyl)-3-ethynyl-5-diethylaminoindene
1-(p-trifluoromethylbenzylidenyl)-3-ethynyl-5-diethylaminoindene
1-(p-bromobenzylidenyl)-3-ethynyl-5-fluoroindene
1-(p-fluorobenzylidenyl)-3-ethynyl-5-fluoroindene
1-(p-nitrobenzylidenyl)-3-ethynyl-5-fluoroindene
1-(p-bromobenzylidenyl)-3-ethynyl-5-methylidene
1-(p-nitrobenzylidenyl)-3-ethynyl-5-methylindene
1-(p-trifluoromethylbenzylidenyl)-3-ethynyl-5-methylindene.

We claim:

1. A compound of the formula

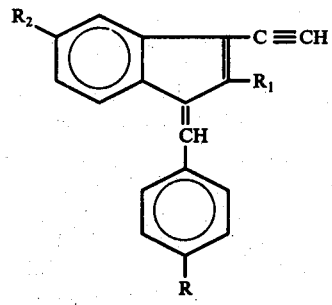

in which
$R_1$ is hydrogen or lower alkyl;
R is cyano or lower alkyl sulfinyl; and
$R_2$ is halo, nitro, lower alkyl, amino, or mono- or di-lower alkylamino.

2. The compound according to claim 1 in which
$R_1$ is lower alkyl;
R is lower alkyl sulfinyl; and
$R_2$ is di-lower alkylamino.

3. The compound of claim 1 in which
$R_1$ is methyl;
R is cyano; and
$R_2$ is nitro.

4. The compound of claim 1 in which
$R_1$ is methyl;
R is methyl sulfinyl; and
$R_2$ is fluoro.

5. A compound of the formula

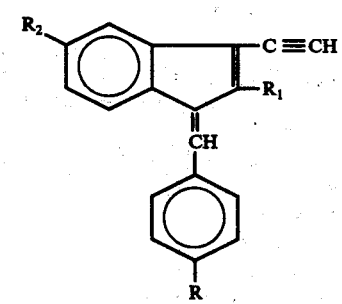

in which
$R_1$ is hydrogen or lower alkyl;
R is halo, nitro, or halo lower alkyl; and
$R_2$ is halo, nitro, lower alkyl, amino, or mono- or di-lower alkylamino.

6. The compound of claim 5 in which
$R_1$ is lower alkyl;
R is halo; and
$R_2$ is di-lower alkylamino.

7. The compound of claim 5 in which
$R_1$ is methyl;
R is chloro; and
$R_2$ is dimethylamino.

8. The compound of claim 5 in which
$R_1$ is methyl;
R is bromo; and
$R_2$ is dimethylamino.

9. The compound of claim 5 in which
$R_1$ is methyl;
R is nitro; and
$R_2$ is dimethylamino.

10. The compound of claim 5 in which
$R_1$ is methyl;

R is fluoro; and
R₂ is dimethylamino.

11. A compound of the formula

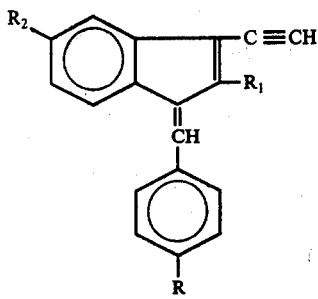

in which
R₁ is hydrogen or lower alkyl;
R is cyano or lower alkyl sulfinyl; and
R₂ is lower alkoxy.

12. The compound of claim 11 in which
R₁ is lower alkyl;
R is lower sulfinyl; and
R₂ is lower alkoxy.

13. The compound of claim 11 in which
R₁ is methyl;
R is methyl sulfinyl; and
R₂ is methoxy.

14. A method for the relief of inflammation in a patient which comprises the administration thereto of a therapeutically effective amount between 0.5 mg. to 100 mg. per kg. of body weight per day of a compound of the formula

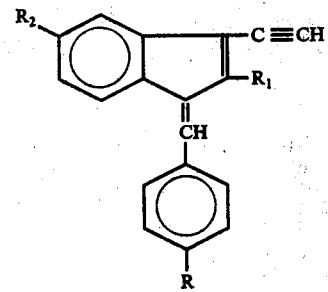

in which
R₁ is hydrogen or lower alkyl;
R is cyano or lower alkyl sulfinyl; and
R₂ is halo, nitro, lower alkyl, amino, or mono- or di-lower alkylamino.

15. The method for the relief of inflammation in a patient by administration of a compound according to claim 14 in which
R₁ is lower alkyl;
R is lower alkyl sulfinyl; and
R₂ is di-lower alkylamino.

16. The method of the relief of inflammation in a patient by administration of a compound according to claim 14 in which
R₁ is methyl;
R is cyano; and
R₂ is nitro.

17. The method of the relief of inflammation in a patient by administration of a compound according to claim 14 in which
R₁ is methyl;
R is methyl sulfinyl; and
R₂ is fluoro.

18. A method for the relief of inflammation in a patient which comprises the administration thereto of a therapeutically effective amount between 0.5 mg. to 100 mg. per kg. of body weight per day of a compound of the formula

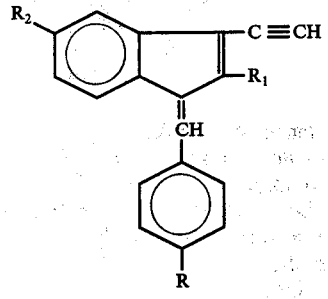

in which
R₁ is hydrogen or lower alkyl;
R is halo, nitro, or halo lower alkyl; and
R₂ is halo, nitro, lower alkyl, amino, or mono- or di-lower alkylamino.

19. The method for the relief of inflammation in a patient by administration of a compound according to claim 18 in which
R₁ is lower alkyl;
R is halo; and
R₂ is di-lower alkylamino.

20. The method for the relief of inflammation in a patient by administration of a compound according to claim 18 in which
R₁ is methyl;
R is chloro; and
R₂ is dimethylamino.

21. The method for the relief of inflammation in a patient by administration of a compound according to claim 18 in which
R₁ is methyl;
R is bromo; and
R₂ dimethylamino.

22. The method for the relief of inflammation in a patient by administration of a compound according to claim 18 in which
R₁ is methyl;
R is nitro; and
R₂ is dimethylamino.

23. The method for the relief of inflammation in a patient by administration of a compound according to claim 18 in which
R₁ is methyl;
R is fluoro; and
R₂ is dimethylamino.

24. A method for the relief of inflammation in a patient which comprises the administration thereto of a therapeutically effective amount between 0.5 mg. to 100 mg. per kg. of body weight per day of a compound of the formula

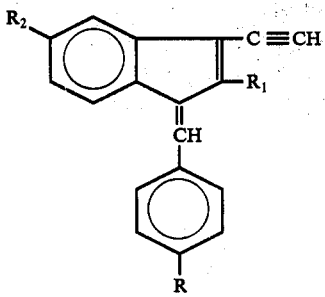

in which
 $R_1$ is hydrogen or lower alkyl;
 R is cyano or lower alkyl sulfinyl; and
 $R_2$ is lower alkoxy.

25. The method for the relief of inflammation in a patient by administration of a compound according to claim 24 in which
 $R_1$ is lower alkyl;
 R is lower alkyl sulfinyl; an
 $R_2$ is lower alkoxy.

26. The method for the relief of inflammation in a patient by administration of a compound according to claim 24 in which
 $R_1$ is methyl;
 R is methyl sulfinyl; and
 $R_2$ is methoxy.

27. A pharmaceutical preparation in dosage unit form suitable for treatment of inflammation, pain or fever comprising a carrier and, as active ingredient, an effective amount of a compound of the formula

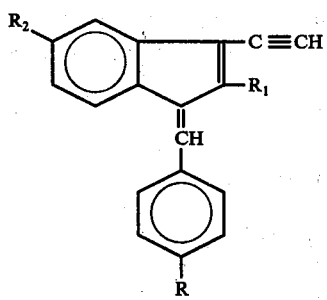

in which
 $R_1$ is hydrogen or lower alkyl;
 R is cyano or lower alkyl sulfinyl; and
 $R_2$ is halo, nitro, lower alkyl, amino, or mono- or di-lower alkylamino.

28. The pharmaceutical preparation according to claim 27 in which
 $R_1$ is lower alkyl;
 R is lower alkyl sulfinyl; and
 $R_2$ is di-lower alkylamino.

29. The pharmaceutical preparation according to claim 27 in which
 $R_1$ is methyl;
 R is cyano; and
 $R_2$ is nitro.

30. The pharmaceutical preparation according to claim 27 in which
 $R_1$ is methyl;
 R is methyl sulfinyl; and
 $R_2$ is fluoro.

31. A pharmaceutical preparation in dosage unit form suitable for the treatment of inflammation, pain, or fever comprising a carrier and, as active ingredient, an effective amount of a compound of the formula:

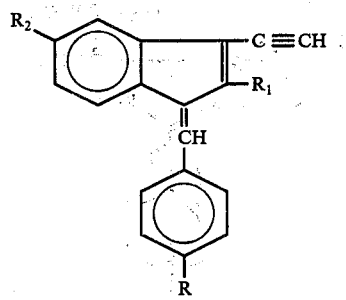

in which
 $R_1$ is hydrogen or lower alkyl;
 R is halo, nitro, or halo lower alkyl; and
 $R_2$ is halo, nitro, lower alkyl, amino, or mono- or di-lower alkylamino.

32. The pharmaceutical preparation according to claim 31 in which
 $R_1$ is lower alkyl;
 R is halo; and
 $R_2$ is di-lower alkylamino.

33. The pharmaceutical preparation according to claim 31 in which
 $R_1$ is methyl;
 R is chloro; and
 $R_2$ is dimethylamino.

34. The pharmaceutical preparation according to claim 31 in which
 $R_1$ is methyl;
 R is bromo; and
 $R_2$ is dimethylamino.

35. The pharmaceutical preparation according to claim 31 in which
 $R_1$ is methyl;
 R is nitro; and
 $R_2$ is dimethylamino.

36. The pharmaceutical preparation according to claim 31 in which
 $R_1$ is methyl;
 R is fluoro; and
 $R_2$ is dimethylamino.

37. A pharmaceutical preparation in dosage unit form suitable for the treatment of inflammation, pain or fever comprising a carrier and, as active ingredient, an effective amount of a compound of the formula

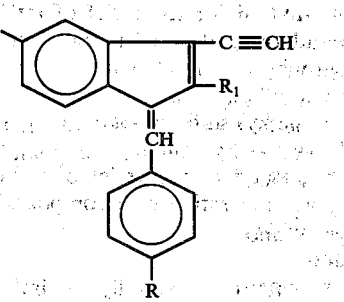

in which
 $R_1$ is hydrogen or lower alkyl;
 R is cyano or lower alkyl sulfinyl; and
 $R_2$ is lower alkoxy.

38. The pharmaceutical preparation according to claim 37 in which
 $R_1$ is lower alkyl;
 R is lower alkyl sulfinyl; and
 $R_2$ is lower alkoxy.

39. The pharmaceutical preparation according to claim 37 in which
 $R_1$ is methyl;
 R is methyl sulfinyl; and
 $R_2$ is methoxy.

* * * * *